(12) United States Patent
Racz (10) Patent No.: US 8,206,343 B2
(45) Date of Patent: Jun. 26, 2012

(54) REINFORCED CATHETER WITH ARTICULATED DISTAL TIP

(75) Inventor: N. Sandor Racz, Coppell, TX (US)

(73) Assignee: Custom Medical Applications, Inc., Johnstown, NY (US)

( * ) Notice: Subject to any disclaimer, the term of this patent is extended or adjusted under 35 U.S.C. 154(b) by 953 days.

(21) Appl. No.: 12/084,529

(22) PCT Filed: Nov. 3, 2006

(86) PCT No.: PCT/US2006/043224
§ 371 (c)(1),
(2), (4) Date: Sep. 16, 2008

(87) PCT Pub. No.: WO2007/056302
PCT Pub. Date: May 18, 2007

(65) Prior Publication Data
US 2009/0043299 A1    Feb. 12, 2009

Related U.S. Application Data (60) Provisional application No. 60/734,706, filed on Nov. 8, 2005.

(51) Int. Cl.
*A61M 31/00* (2006.01)
*A61M 37/00* (2006.01)
*A61B 17/20* (2006.01)
*A61M 25/00* (2006.01)

(52) U.S. Cl. .................. 604/95.01; 604/95.04; 604/528; 604/22

(58) Field of Classification Search ............... 604/95.04, 604/95.01, 528, 22
See application file for complete search history.

(56) References Cited

U.S. PATENT DOCUMENTS

| 3,470,876 A | 10/1969 | Barchilon |
| 3,892,228 A | 7/1975 | Mitsui |
| 4,719,924 A | 1/1988 | Crittenden et al. |
| 4,898,577 A | 2/1990 | Badger et al. |

(Continued)

FOREIGN PATENT DOCUMENTS

JP    2000-126301    5/2000

(Continued)

OTHER PUBLICATIONS

Notice of Reasons for Rejection for copending Japanese Patent Application No. 2008-540103 with set of pending claims, dated Sep. 2011.

(Continued)

*Primary Examiner* — Christopher D Koharski
*Assistant Examiner* — Ian Holloway
(74) *Attorney, Agent, or Firm* — TraskBritt (57) ABSTRACT

A reinforced medical catheter (10) includes an elongated tubular outer wall reinforced by an internal helical coil spring (36). Successive loops of the coil spring adjoining the distal end are longitudinally separated, and a working lumen extends longitudinally through the catheter. A longitudinally extending reinforcing cable is captured in the tubular outer wall against the exterior of the coil spring. A steering cable operably interconnected with the distal end of the coil spring extends proximally from the distal end of the coil spring freely through the working lumen to the proximal end of the catheter. The reinforcing cable and the steering cable may constitute a continuous elongated filament. Withdrawing the steering cable proximally through the working lumen causes the distal tip of the catheter to be deflected laterally.

25 Claims, 8 Drawing Sheets

U.S. PATENT DOCUMENTS

| | | | |
|---|---|---|---|
| 4,921,482 | A | 5/1990 | Hammerslag et al. |
| 4,985,022 | A | 1/1991 | Fearnot et al. |
| 4,998,916 | A | 3/1991 | Hammerslag et al. |
| 5,002,041 | A * | 3/1991 | Chikama ............ 600/139 |
| 5,037,391 | A | 8/1991 | Hemmerslag et al. |
| 5,108,368 | A | 4/1992 | Hammerslag et al. |
| 5,203,772 | A | 4/1993 | Hemmerslag et al. |
| 5,254,088 | A | 10/1993 | Lundquist et al. |
| 5,336,182 | A | 8/1994 | Lundquist et al. |
| 5,342,299 | A | 8/1994 | Snoke et al. |
| 5,364,351 | A | 11/1994 | Heinzelman et al. |
| 5,372,587 | A * | 12/1994 | Hammerslag et al. ..... 604/95.04 |
| 5,378,234 | A | 1/1995 | Hammerslag et al. |
| 5,389,073 | A | 2/1995 | Imran |
| 5,391,147 | A | 2/1995 | Imran et al. |
| 5,395,327 | A | 3/1995 | Lundquist et al. |
| 5,395,328 | A | 3/1995 | Ockuly et al. |
| 5,397,304 | A * | 3/1995 | Truckai ............ 604/528 |
| 5,431,168 | A | 7/1995 | Webster, Jr. |
| 5,456,664 | A | 10/1995 | Heinzelman et al. |
| 5,478,330 | A | 12/1995 | Imran et al. |
| 5,484,407 | A | 1/1996 | Osypka |
| 5,520,222 | A | 5/1996 | Chikama |
| 5,531,686 | A | 7/1996 | Lundquist et al. |
| 5,533,967 | A | 7/1996 | Imran |
| 5,588,964 | A | 12/1996 | Imran et al. |
| 5,656,029 | A | 8/1997 | Imran et al. |
| 5,792,074 | A | 8/1998 | Turkel et al. |
| 5,797,842 | A | 8/1998 | Pumares et al. |
| 5,803,083 | A | 9/1998 | Buck et al. |
| 5,876,373 | A | 3/1999 | Giba et al. |
| 6,027,473 | A | 2/2000 | Ponzi |
| 6,030,360 | A | 2/2000 | Biggs |
| 6,033,378 | A | 3/2000 | Lundquist et al. |
| 6,120,476 | A | 9/2000 | Fung et al. |
| 6,123,699 | A | 9/2000 | Webster, Jr. |
| 6,126,649 | A | 10/2000 | VanTassel et al. |
| 6,146,355 | A | 11/2000 | Biggs |
| 6,171,277 | B1 | 1/2001 | Ponzi |
| 6,183,463 | B1 | 2/2001 | Webster, Jr. |
| 6,213,974 | B1 | 4/2001 | Smith et al. |
| 6,224,587 | B1 | 5/2001 | Gibson |
| 6,491,681 | B1 | 12/2002 | Kunis et al. |
| 6,500,167 | B1 | 12/2002 | Webster, Jr. |
| 6,530,913 | B1 | 3/2003 | Giba et al. |
| 6,554,794 | B1 * | 4/2003 | Mueller et al. ............ 604/95.04 |
| 6,579,279 | B1 | 6/2003 | Rabiner et al. |
| 6,585,718 | B2 | 7/2003 | Hayzelden et al. |
| 6,648,875 | B2 | 11/2003 | Simpson et al. |
| 6,783,510 | B1 | 8/2004 | Gibson et al. |
| 6,860,876 | B2 | 3/2005 | Chen |
| 7,128,718 | B2 * | 10/2006 | Hojeibane et al. ............ 600/585 |
| 7,763,012 | B2 * | 7/2010 | Petrick et al. ................ 604/527 |
| 2005/0049574 | A1 | 3/2005 | Petrick |
| 2005/0209557 | A1 * | 9/2005 | Carroll et al. .............. 604/95.04 |

FOREIGN PATENT DOCUMENTS

| | | |
|---|---|---|
| JP | 2001-009042 | 1/2001 |
| WO | WO 2007/056302 A2 | 11/2006 |

OTHER PUBLICATIONS

PCT International Search Report and Written Opinion, PCT/US06/43224 dated Apr. 30, 2007.

Supplementary Partial European Search Report for EP 06 82 7576.7, mailed Sep. 1, 2010, 15 pages.

* cited by examiner

REINFORCED CATHETER WITH ARTICULATED DISTAL TIP

PRIORITY CLAIM

This application is the National Phase entry of PCT International Application Number PCT/US2006/043224, filed on Nov. 3, 2006, and published, in English, as WO 2007/056302 A2 on May 18, 2007. This application claims the benefit of the filing date of U.S. Provisional Patent Application Ser. No. 60/734,706, filed Nov. 8, 2005, for "Reinforced Catheter with Articulated Distal Tip", the contents of which are incorporated herein by this reference.

TECHNICAL FIELD

The invention pertains to catheter tubes with distal tips that are so articulated as to be laterally selectively deflectable and to the longitudinal reinforcement of the tubing used in such catheters and means and methods of making and using such catheter tubes. More particularly, the invention relates to articulated distal tips in longitudinally reinforced catheters of relatively self-sustaining structure, such as epidural catheters.

DESCRIPTION OF THE DRAWINGS

The manner in which the advantages of the invention are obtained will be understood by a particular description of the invention rendered by reference to specific embodiments thereof that are illustrated in the appended drawings. Understanding that these drawings depict only typical embodiments of the invention and are not therefore to be considered limiting of its scope, the invention will be described and explained with specificity and detail through the use of the accompanying drawings in which.

MODE(S) FOR CARRYING OUT THE INVENTION

Figure 1:
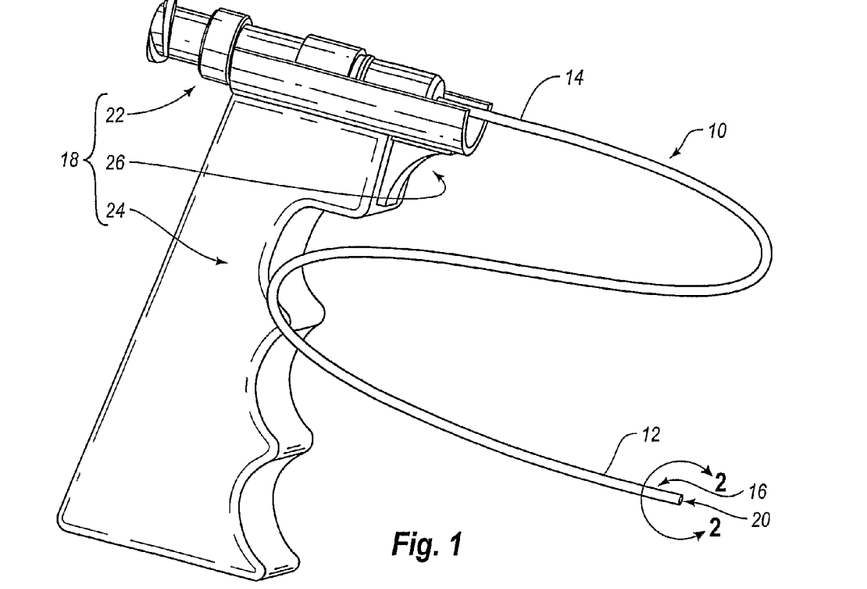
FIG. 1 is a perspective view of a first embodiment of a catheter embodying teachings of the invention, having an articulated distal tip, and being attached to a user handle to facilitate extracorporeal use by medical personnel.

FIG. 1 depicts a first embodiment of a flexible catheter 10 having an open distal end 12 and a proximal end 14 and incorporating teachings of the invention. Catheter 10 is a reinforced catheter having an articulated distal tip 16 at distal end 12 thereof that can be selectively deflected laterally into and out of the longitudinally aligned position of distal tip 16 shown in FIG. 1. This deflection is accomplished by the selective displacement of structures interior of catheter 10 that are actuated by mechanisms of a user handle 18 to which proximal end 14 of catheter 10 is attached. The articulation of distal tip 16 is advantageous in facilitating the accurate placement of the terminus 20 of distal tip 16 at a predetermined location in the body of a patient at which an intended therapeutic activity is to be conducted. Depending upon the uses to which catheter 10 is intended to be applied, such therapeutic activity might include the infusion of medication or the aspiration of body fluids, the visualization of regions interior the body of the patient, the measurement of internal body conditions, or the subjugation of regions of the interior of the body of a patient to cauterization or radio frequency ("RF") heating, pulsed RF, and electrical nerve stimulation.

Catheter 10 encloses a longitudinally extending working lumen that communicates with the exterior of catheter 10 at terminus 20 of distal tip 16. As used herein the expression "working lumen" is intended to connote a passageway interior of a catheter that is used to conduct or facilitate therapeutic activities other than or in addition to those related to the implantation, positioning, or orientation of the catheter or the distal tip thereof. In particular, a catheter passageway dedicated specifically to purposes pertaining to the implantation, positioning, or orientation of a catheter or the distal tip thereof, to the exclusion of any therapeutic activity, is not intended to be included within the scope of the expression "working lumen" as used herein.

User handle 18 includes a connection hub 22 attached to proximal end 14 of catheter 10. Connection hub 22 enables selective fluid communication to be established by way of the working lumen in catheter 10 with the region interior the body of a patient at which terminus 20 of distal tip 16 is disposed. Nonetheless, the teachings of the invention have utility in a catheter having a working lumen with a closed distal end or a working lumen that communicates with the exterior of that catheter through the sidewalls thereof. In any case, connection hub 22 of user handle 18 is secured to a hand grip 24 that includes a moveable finger trigger 26 by which lateral deflection of distal tip 16 is selectively controlled by a medical practitioner.

The structure of catheter 10 is reinforced for several purposes. The first of these is to preclude failure in the structural integrity of catheter 10 during use, either within or outside of the body of a patient. Thus, it is intended through such reinforcement that the shaft of catheter 10 be precluded from unintentional kinking, that distal tip 16 of catheter 10 be incapable of separation from the balance of the shaft of catheter 10, and that the outer wall of catheter 10 be prevented from puncture or rupture. Second, catheter 10 is sufficiently reinforced as to be able, once distal end 12 of catheter 10 has been entered into the body of a patient, to transmit to distal tip 16 forces applied by medical practitioners to proximal end 14 of catheter 10 to effect the advancement, the withdrawal, or the rotation of catheter 10.

While the various teachings of the invention disclosed herein find full utility in catheters utilizable in epidural procedures, those teachings also have applicability in whole or in part in all types of medical catheters, including cardiovascular access catheters, coronary catheters, endoscopic catheters, and surgical catheters.

Figure 2:
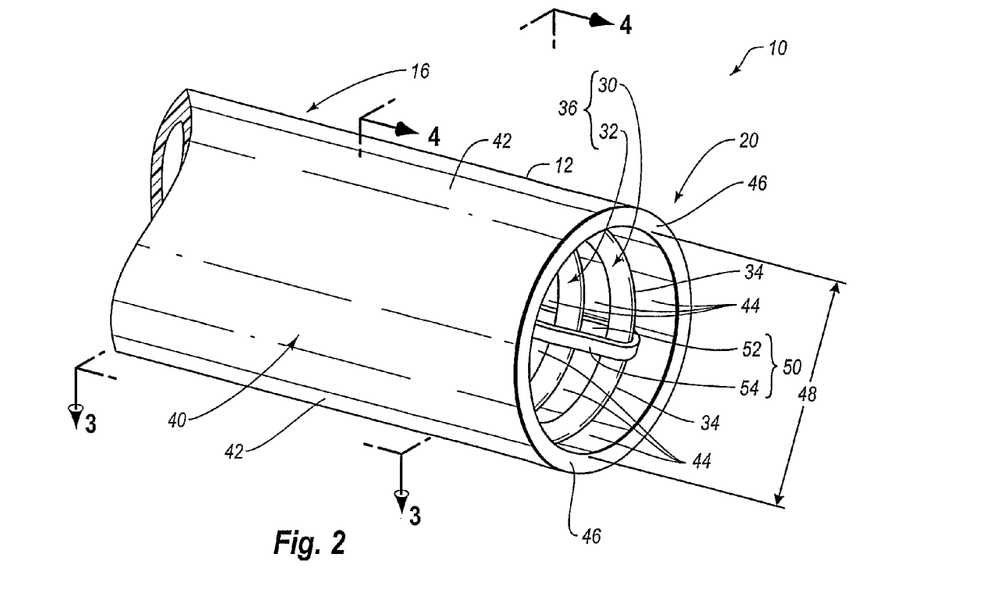
FIG. 2 is an enlarged perspective view of the distal tip of the catheter of FIG. 1.

FIG. 2 is a greatly enlarged perspective view of distal tip 16 of catheter 10 taken from terminus 20 of distal tip 16 in such a manner as to begin to reveal internal structural aspects of catheter 10. There, for example, can be seen that catheter 10 is a generally hollow cylindrical structure having an open end at terminus 20 of distal tip 16 through which access is afforded to the space interior of catheter 10. Visible through the open end of terminus 20 is the distal end 34 of an elongated helical coil spring 36, including a final loop 30 and a penultimate loop 32 thereof. The successive loops of coil spring 36 encircle a longitudinal passageway that extends from distal end 34 of coil spring 36 through the full length of coil spring 36 to user handler 18. The passageway enclosed by coil spring 36 thus corresponds substantially to the working lumen in catheter 10.

Figures 3, 4:
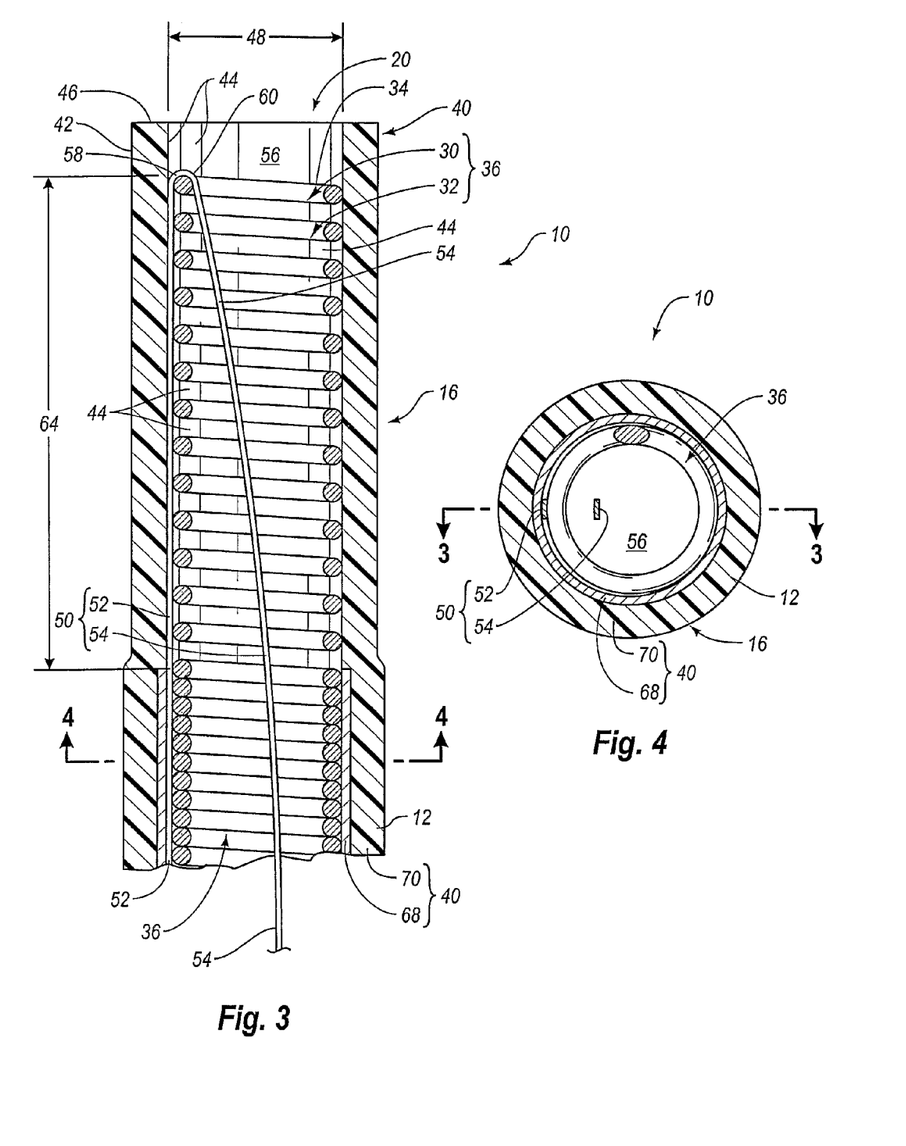
FIG. 3 is a longitudinal cross section of the distal tip of the catheter illustrated in FIG. 2 taken along section line 3-3 shown therein.
FIG. 4 is a transverse cross sectional view of the distal tip of the catheter of FIG. 2 taken along section line 4-4 shown therein.

A cylindrical, flexible tube 40, comprising layer 68 and layer 70, snugly engages the exterior surfaces of the successive loops of coil spring 36 through at least terminal portion 64 of coil spring 36 (explained in reference to FIG. 3). In an embodiment, layer 68 is about 0.001" in depth or thickness and layer 70 is about 0.005" in depth or thickness. Flexible tube 40 has outer walls of uniform thickness, a cylindrical outer surface 42, a correspondingly shaped but slightly smaller interior surface 44 through at least terminal portion 64. Layer 68 does not cover coil spring 36 past terminal portion 64. Layer 68 ends proximal to terminal portion 64 of coil spring 36 and outer surface 42 ends at terminus 20 of distal tip 16. End face 46 is oriented normal to the longitudinal axis of catheter 10 at terminus 20 of distal tip 16. Catheters incorporating teachings of the invention need not, like catheter 10, be circular in outer cross section or possessed of outer walls of uniform thickness. Coil springs of an appropriate noncircular cross section are also not unknown and would be capable of use in noncircular catheters under such alternative circumstances.

Flexible tube 40 is constructed of various medical grade materials, such as PET, FEP, nylon, urethane, silicone, or other polymers in a uniform matrix or in a layered arrangement of materials.

Final loop 30 and penultimate loop 32 of coil spring 36 are longitudinally separated from each other. This is also the case in relation to penultimate loop 32 and the next successive loop of distal end 34 that is not visible in FIG. 2, but that will in subsequent FIGs. be revealed to be proximally disposed relative to penultimate loop 32 on the opposite side thereof from final loop 30. Accordingly, portions of inner surface 44 of flexible tube 40 are visible in FIG. 2 through the longitudinal spaces between the successive longitudinally separated loops of coil spring 36.

Flexible tube 40 precludes lateral access to or from the working lumen extending longitudinally through catheter 10 and the center of coil spring 36. Communication of that working lumen with the exterior of catheter 10 is thus restricted to a circular end opening 48 that is encircled by end face 46 of flexible tube 40.

The circularity of an end opening, such as end opening 48, is not, however, essential to the effective implementation of teachings of the invention. Catheters with noncircular exterior cross sections or with end openings inclined relative to the longitudinal axis of a catheter at the distal terminus thereof will in most instances have end openings that are not circular. Circumstances exist relative to specific intended medical procedures in which the distal tip structure of a catheter may vary from the structure of the balance of the body of the catheter, often toward the end of effecting a particular distal end opening configuration. In addition, catheters are known in which the working lumen thereof is closed at the distal end thereof; so that fluid flow therethrough is precluded, or if effected at all, is effected through apertures or valving provided in the side walls or the tip of the catheter.

Snugly engaged by flexible tube 40, the successive loops of coil spring 36 add to the robustness of catheter 10, increasing resistance to kinking or collapse and improving the degree to which advancement, retraction, and torsional forces applied to proximal end 14 of catheter 10 are transmitted to distal tip 16 thereof when distal end 12 of catheter 10 is resident in the body of a patient. Thus, coil spring 36 and flexible tube 40 in combination function as an elongated tubular outer wall for catheter 10 that is internally reinforced by a helical coil spring.

According to one aspect of the invention, a catheter, such as catheter 10 is provided with utility enhancement means operably interconnected with the outer wall of that catheter. The utility enhancement means of the invention performs the dual functions of longitudinally rigidifying the outer wall of that catheter and of selectively laterally deflecting the distal tip thereof. In the context of catheter 10, such a utility enhancement means is operably interconnected to both coil spring 36 and to flexible tube 40.

As seen in part in FIG. 2 and more completely in the longitudinal cross section of distal tip 16 shown in FIG. 3, an example of a structure capable of performing the functions of such a utility enhancement means takes the form of a continuous filament 50 having a bound portion 52 extending longitudinally between flexible tube 40 and the exterior of coil spring 36 and a free portion 54 that extends freely through a working lumen 56 in catheter 10.

While the proximal end of bound portion 52 of filament 50 is not shown in FIG. 3, the distal end 58 of bound portion 52 is disposed in proximity to final loop 30 of coil spring 36. Bound portion 52 of filament 50 is permanently captured between flexible tube 40 and the exterior of coil spring 36, and being incapable of being withdrawn from therebetween, is operably interconnected to both coil spring 36 and to flexible tube 40. As a result, bound portion 52 of filament 50 adds to the longitudinal rigidity of catheter 10. Where bound portion 52 of filament 50 extends proximally from distal end 58 thereof through the full length of catheter 10 to proximal end 14 thereof, the enhanced longitudinal rigidity imparted to catheter 10 by bound portion 52 improves the capability of the shaft of catheter 10 to communicate to distal tip 16 thereof any advancement, withdrawal, and twisting forces applied to proximal end 14 of catheter 10 during use.

Free portion 54 of filament 50 has a distal end 60 that is secured in a smoothly continuous maimer to distal end 58 of bound portion 52. As a result free portion 54 is also operably interconnected to both spring coil 36 and to flexible tube 40.

Filament 50 is constructed from a medical grade metallic or synthetic material having substantial tensile strength. As seen in the transverse cross section in FIG. 4, each of bound portion 52 and free portion 54 of filament 50 has a generally flat, rectangular cross section, although other cross-sectional shapes in a filament, such as filament 50, would function successfully in the context of the invention. Additionally, the cross-sectional configuration of such a filament need not be uniform throughout the full length thereof.

Figure 5A:
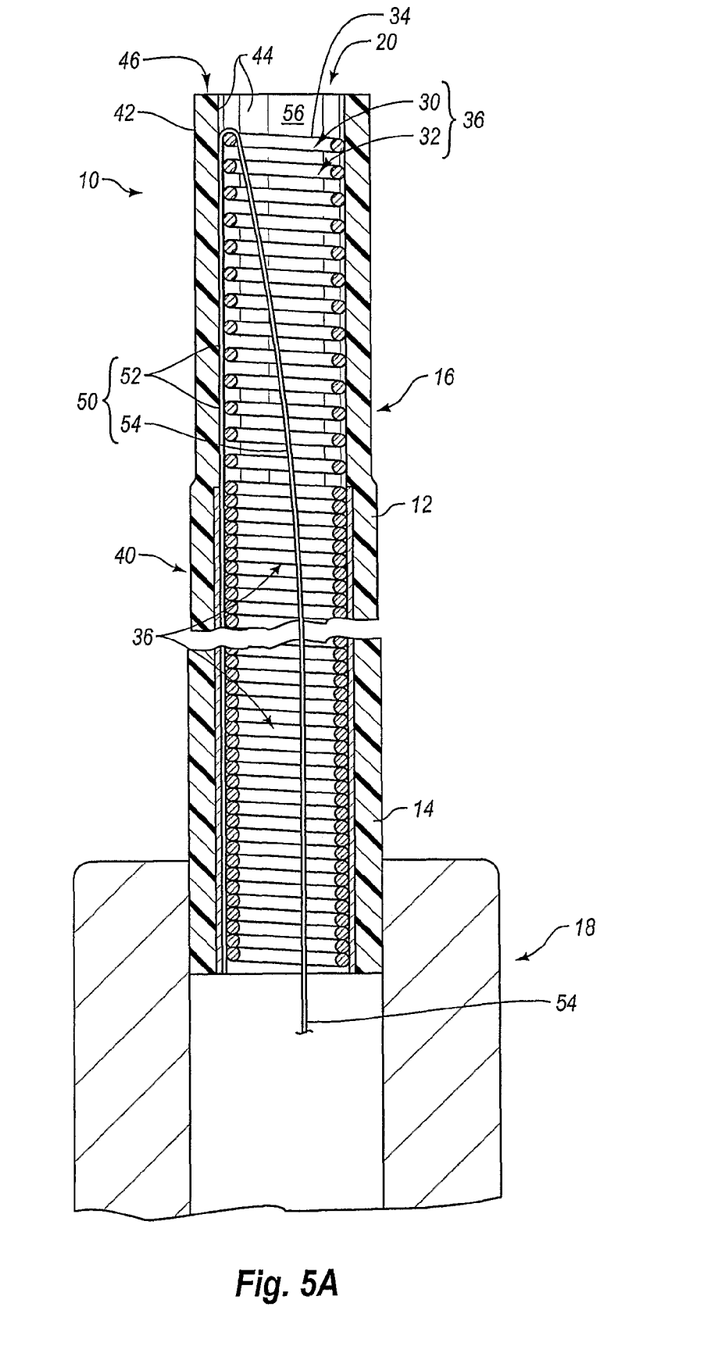
FIG. 5A is a longitudinal cross section of the catheter of FIG. 1 similar to that shown in FIG. 3 and including portions of the catheter tube of FIG. 1 adjacent to the user handle of FIG. 1.

As shown in FIG. 5A, free portion 54 of filament 50 extends from distal end 60 of free portion 54 proximally through the full length of working lumen 56 to proximal end 14 of catheter 10. There in the interior of user handle 18, free portion 54 is coupled to structures that serve to selectively draw free portion 54 of filament 50 in a proximal direction through working lumen 56. The mechanisms by which this can be accomplished interior of user handle 18 are numerous and will not be depicted or disclosed in detail.

Figure 5B:
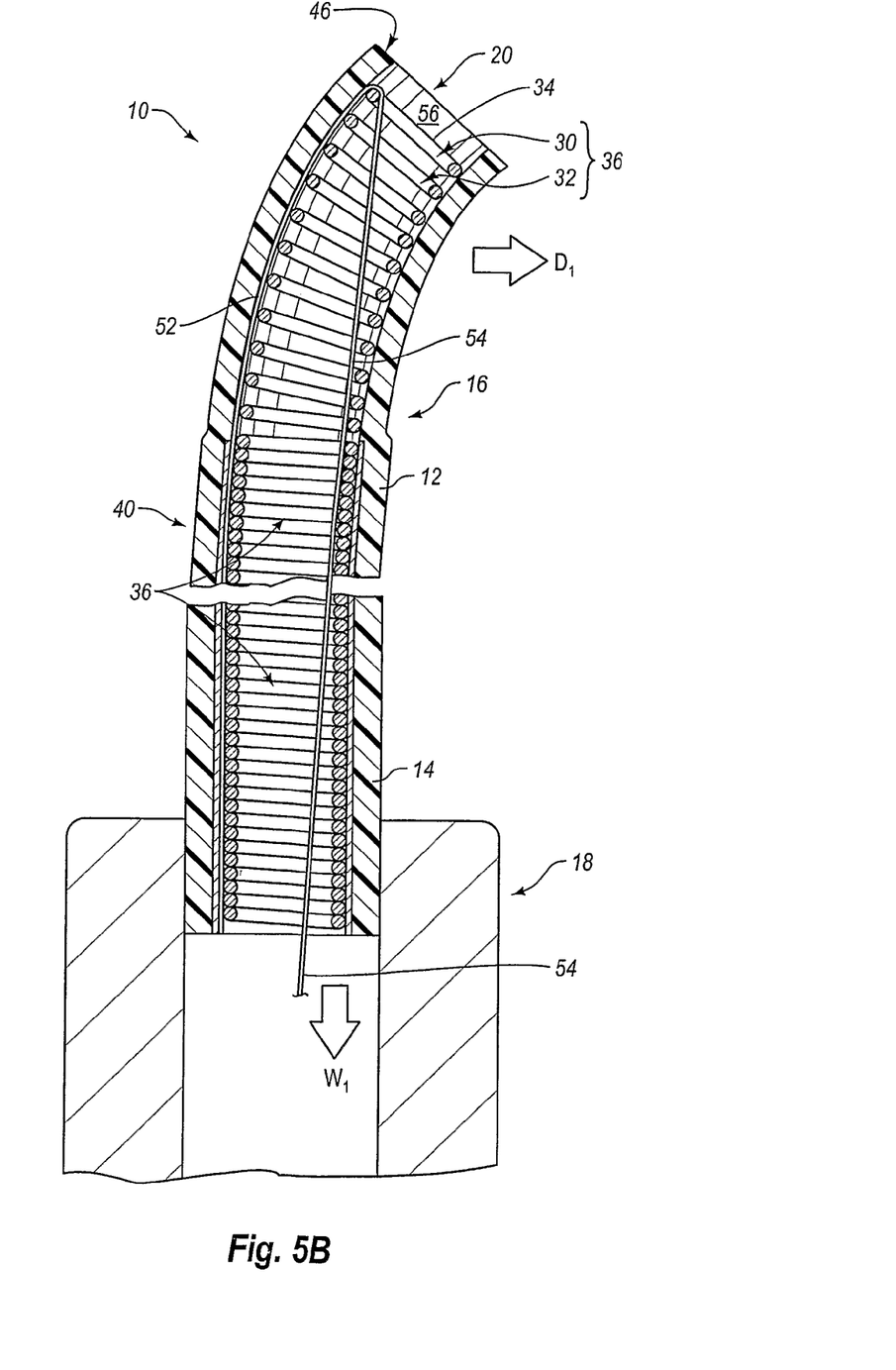
FIG. 5B is a longitudinal cross section like that in FIG. 5A in which the distal tip of the illustrated catheter has been directed to the right as shown in FIG. 5B due to the selective displacement of interior elements of the catheter and user handle shown in FIG. 1.

Nonetheless, as depicted in FIG. 5B, drawing free portion 54 of filament 50 in a proximal direction identified by an arrow $W_1$ has the effect of transmitting to penultimate loop 32 of coil spring 36 a proximally directed forced that in turn causes distal tip 16 of catheter 10 to be deflected laterally from the longitudinally aligned position illustrated in FIG. 5A toward the right as indicated by an arrow $D_1$ in FIG. 5B. Thus, distal tip 16 of catheter 10 is selectively steerable from proximal end 14 thereof. In that selectively articulatable condition, distal tip 16 of catheter 10 may be readily oriented and positioned at any predetermined location inside the body of the patient at which therapeutic activity is to be conducted. If it is intended to deflect distal tip 16 in the opposite direction, to the left in FIG. 5A, then catheter 10 is first rotated by 180° through the application of twisting forces to proximal end 14 of catheter 10. Then the retraction of free portion 54 of filament 50 through working lumen 56 in the direction of arrow $W_1$ will cause distal tip 16 to be deflected to the left in FIG. 5A.

As shown in FIG. 3, the longitudinal separation between successive loops of coil spring 36 within the embrace of flexible tube 40 is repeated through a terminal portion 64 of coil spring 36 adjoining distal end 34 thereof. This arrangement increases the lateral flexibility in catheter 10 at terminal portion 64 of coil spring 36, and that in turn facilitates steering movements of the type illustrated in FIG. 5B. Proximal of terminal portion 64 of coil spring 36 successive loops of coil spring 36 are in adjacent abutment to each other, a condition that will be referred to herein as being "bottomed out." The portion of coil spring 36 that is bottomed out affords to catheter 10 less lateral flexibility than is afforded in the portion of catheter 10 that encircles terminal portion 64 of coil spring 36. The portion of catheter 10 that encircles terminal portion 64 of coil spring 36 is readily deflectable laterally. This reduces the likelihood of injury by that portion of catheter 10 to internal physiological structures in the body of a patient.

If a substantial length of distal end 12 of catheter 10 is free from constraints by internal physiological structures within the body of a patient, the proximal withdrawal of free portion 54 of filament 50 will initially cause only the portion of catheter 10 surrounding distal portion 64 of coil spring 36 to deflect laterally as shown in FIG. 5B. Therefore, the portion of distal tip 16 of catheter 10 that engages in articulated lateral movement will most generally correspond to the portion of catheter 10 at terminal portion 64 of coil spring 36.

There are many types of catheters in which no substantial portion of a reinforcing internal helical coil spring is bottomed out in the manner illustrated in FIG. 3. In such structures, the drawing of free portion 54 of filament 50 in a proximal direction will tend to induce the entirety of the distal end of the corresponding catheter that is free from lateral constraint by internal physiological structures to deflect laterally as shown in FIG. 5B. This would not be inconsistent with the teachings of the invention.

On occasion, flexible tube 40 is constructed as a plurality of concentric layers. Such a situation is illustrated in FIGS. 3 and 4, where flexible tube 40 can be seen to comprise an inner layer 68 disposed in direct contact with the exterior of coil spring 36 and an outer layer 70 that engages the exterior of inner layer 68. Typically, inner layer 68 is a tough biocompatible flexible plastic material that can be heat shrunk onto the exterior of coil spring 36, while outer layer 70 is made of a softer, flexible, more skin-compatible material, thereby to afford a comfortable interface with bodily tissue. Layer 68 is more rigid than layer 70 for longitudinal stability and catheter torque.

To manufacture a catheter, such as catheter 10, a first portion of a filament, such as filament 50, is disposed along the exterior of an elongated, helical coil spring, such as coil spring 36. This assembly is then placed in an oversized heat-shrinkable polyester tube. Heat is applied to the assembly, causing the polyester tube to snuggly engage the exterior of the coil spring with the first portion of the filament captured therebetween. A second portion of the filament not otherwise thusly captured is then passed through the passageway in the spring coil from one end to the other. Finally, an outer layer of skin compatible material is applied to the exterior of the polyester tube using extrusion over-molding techniques.

Figure 6:
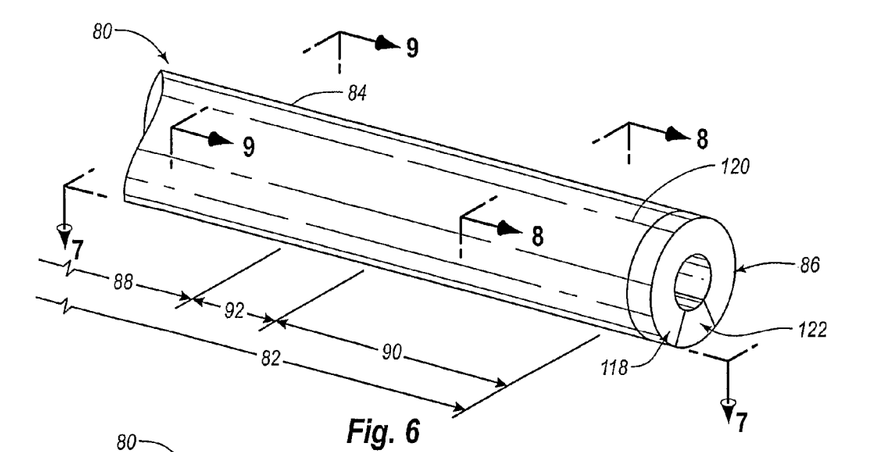
FIG. 6 is an enlarged perspective view of the distal tip of a second embodiment of a catheter incorporating teachings of the invention.

FIG. 6 is an enlarged perspective view of a second embodiment of a catheter 80 embodying teachings of the invention. Catheter 80 has a distal tip 82 at distal end 84 thereof. The proximal end of catheter 80, which is not shown, is attachable to a user handle, such as user handle 18 shown in FIG. 1. From FIG. 6, it can be seen that catheter 80 is a generally hollow cylindrical structure having an open end at terminus 86 of distal tip 82 through which access is afforded to the space interior of catheter 80. The space interior of catheter 80 functions as a working lumen extending longitudinally through catheter 80. Distal end 84 of catheter 80 exhibits a two-stage exterior profile that includes a relatively larger diameter proximal portion 88 and a smaller diameter distal portion 90 interconnected by an external smoothly continuous transition portion 92 wherein the two portions are not overtly visibly tapered. This results in a differential in flexibility along the length of distal tip 82 of catheter 80 and a maximum flexibility at distal portion 90.

Figure 7:
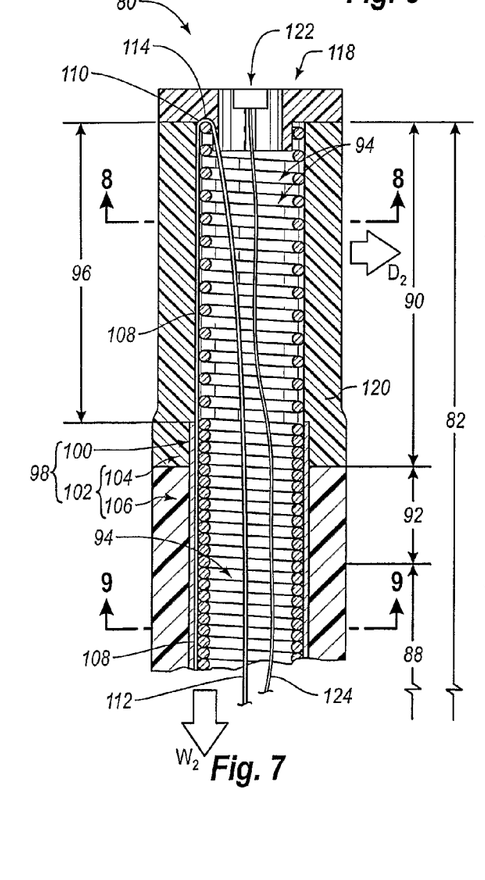
FIG. 7 is a longitudinal cross section of the distal tip of the catheter of FIG. 6 taken along section line 7-7 shown therein.

The longitudinal cross section presented in FIG. 7 reveals that the outer wall of catheter 80 at distal tip 82 includes an elongated helical coil spring 94 having an open distal end and enclosing a passageway extending longitudinally therethrough. In a terminal portion 96 of coil spring 94 adjoining the distal end thereof, successive loops of coil spring 94 are longitudinally separated. Proximal of terminal portion 96 successive loops of coil spring 94 are bottomed out.

An elongated flexible tube 98 snugly engages the exterior of coil spring 94, whereby flexible tube 98 and coil spring 94 together function as an elongated tubular outer wall for catheter 80 that is internally reinforced by a helical coil spring. Flexible tube 98 includes an inner layer 100 that is disposed in direct contact with the exterior of coil spring 94 and an outer layer 102 that engages the exterior of inner layer 100. Often, outer layer 102 is made softer, or more skin compatible, than inner layer 100. Furthermore, a terminal portion 104 of outer layer 102 adjoining the distal end of outer layer 102 is made of softer material than is the longitudinal balance 106 of outer layer 102 proximal of terminal portion 104. This results in a differential in flexibility along the length of distal tip 82 of catheter 80 and a maximum flexibility at terminal position 104 of outer layer 102.

Figure 8:
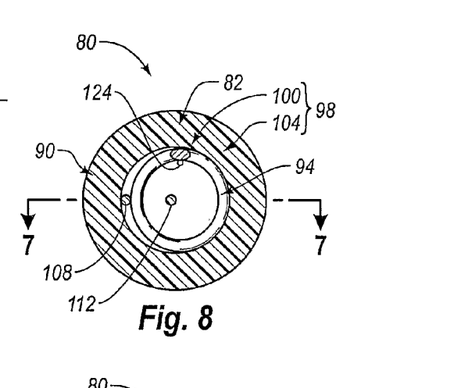
FIG. 8 is a transverse cross section of the distal tip of the catheter shown in FIG. 6 taken along section line 8-8 shown therein.
Figure 9:
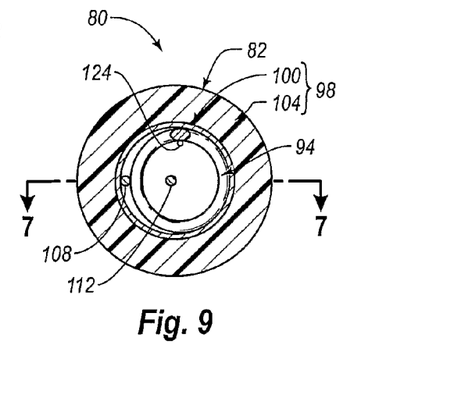
FIG. 9 is a transverse cross section of the distal tip of the catheter shown in FIG. 6 taken along section line 9-9 shown therein.

These relationships are depicted in transverse cross section in FIGS. 8 and 9. There, each of reinforcing cable 108 and steering cable 112 is seen to have a circular cross section, although other cross-sectional shapes in such structures would function successfully in the context of the invention. Additionally, the cross-sectional configuration of reinforcing cable 108 may differ from the cross-sectional configuration of steering cable 112 and may be nonuniform along the respective lengths thereof.

As shown in FIG. 7, terminal portion 104 of outer layer 102 coincides with small-diameter distal portion 90 of distal tip 82 of catheter 80. Nonetheless, if the terminal portion of the outer layer of a catheter constructed according to teachings of the invention is made softer than the longitudinal balance of that outer layer, the transition from soft to less soft material in the outer layer need not occur at a longitudinal location along the catheter at which there is a change in the outer diameter of that catheter.

According to one aspect of the invention, a catheter, such as catheter 80 includes utility enhancement means operably interconnected with the outer wall of the catheter for both longitudinally rigidifying the outer wall and for selectively laterally deflecting the distal tip of the catheter. As illustrated in FIG. 7, by way of example and not limitation, catheter 80 includes a longitudinally extending reinforcing cable 108 captured against the exterior of coil spring 94 by inner layer 100 of flexible tube 98. The distal end 110 of reinforcing cable 108 is disposed in proximity to the distal end of coil spring 94. Catheter 80 also includes a steering cable 112 having a distal end 114 that is connected with distal end 110 of reinforcing cable 108. Steering cable 112 extends freely through the working lumen within catheter 80 to the proximal end thereof, which is not shown in FIG. 7. The withdrawal of steering cable 112 proximally within the working lumen in catheter 80 as indicated by an arrow $W_2$ causes distal tip 82 of catheter 80 to deflect laterally toward the right in a direction indicated by an arrow $D_2$. In various embodiments, steering cable 112, reinforcement cable 108, and/or filament 146 increase radiopacity of the embodiment, thereby allowing for better visibility when using fluoroscopic guidance or the like.

If it is intended to deflect distal tip 82 in the opposite direction, to the left in FIG. 7, distal tip 82 of catheter 80 is first rotated by 180° through the application of twisting forces to the proximal end of catheter 80. Then the withdrawal of steering cable 112 through the working lumen in catheter 80 in the direction of arrow $W_2$ will cause distal tip 82 to be deflected to the left in FIG. 7.

Distal end 114 of steering cable 112 is connected to distal end 110 of reinforcing cable 108 in a smoothly continuous manner, whereby reinforcing cable 108 and steering cable 112 are a continuous elongated structure. Nonetheless, steering cable 112 and reinforcing cable 108 could be distinctly different structures with attached distal ends or with distal ends operably interconnected through intermediating structures.

At terminus 86 of distal tip 82 of catheter 80 is a rigid end piece 118 that is secured to distal end 120 of flexible tube 98. As appreciated by reference to FIG. 7, end piece 118 is a ring coaxially disposed relative to the working lumen within catheter 80. An electrical transducer 122 is carried by end piece 118 and coupled electrically to circuitry at the proximal end of catheter 80 by a lead wire 124 that extends proximally from transducer 122 through the working lumen in catheter 80. Transducer 122 is capable of selectively performing any of various therapeutical medical functions, such as cauterization or heating of tissue within the body of a patient at distal terminus 86 of distal tip 82 of catheter 80. To optimally position distal tip 82 for such therapeutic activity, steering cable 112 is manipulated as previously described.

End piece 118 can also function as an attachment site for the distal ends of one or both of reinforcing cable 108 and steering cable 112. Where reinforcing cable 108 and steering cable 112 are a continuous elongated structure, that structure can be looped through an end piece, such as end piece 118, in order to implement teachings of the invention.

Figure 10:
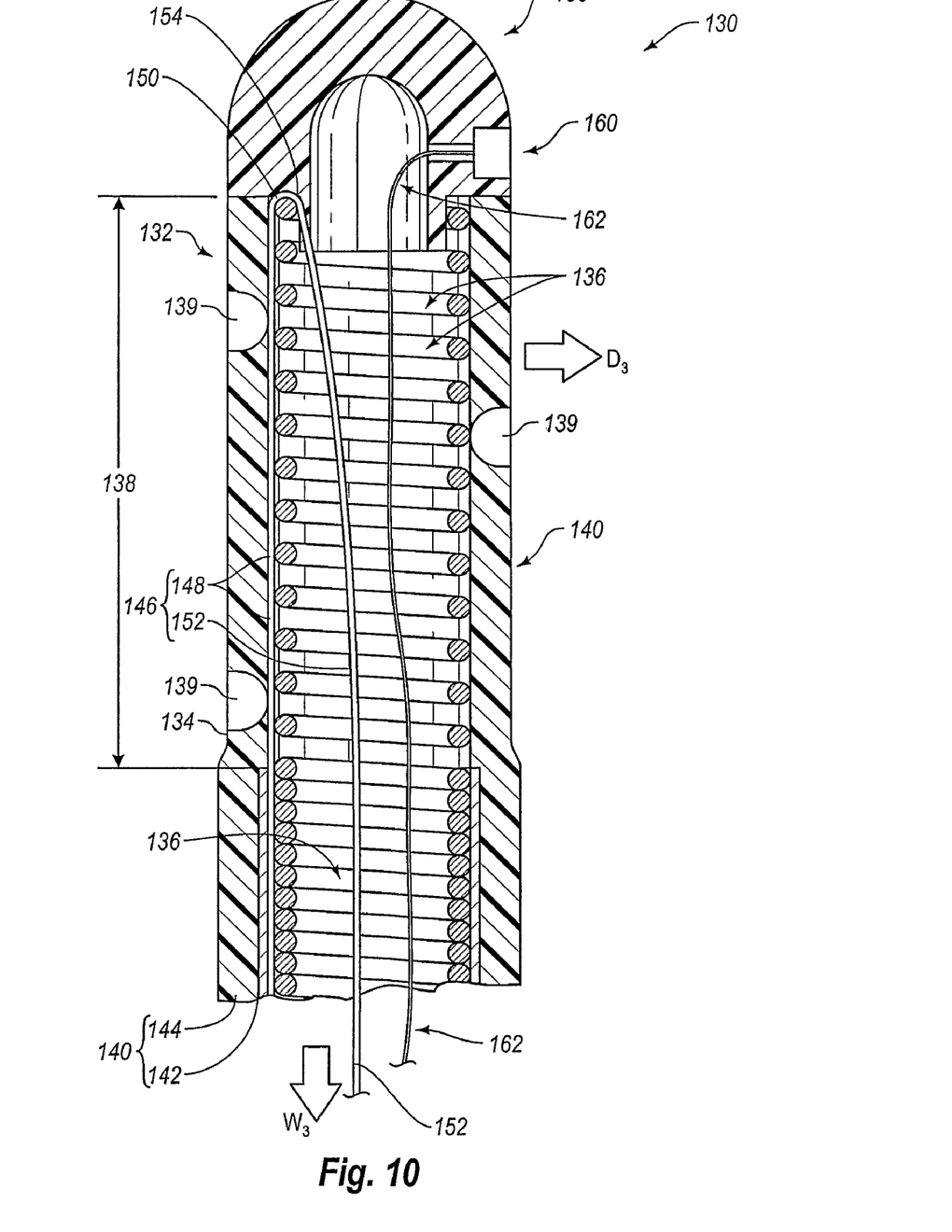
FIG. 10 is a longitudinal cross section similar to that of FIG. 7 of a third embodiment of a distal tip of a catheter incorporating teachings of the invention.

FIG. 10 is a longitudinal cross section of the distal end of a third embodiment of a catheter 130 incorporating teachings of the invention. Catheter 130 has a distal tip 132 at distal end 134 thereof that is articulatable. Although not shown in FIG. 10, the proximal end of catheter 130 may be secured to a user handle, such as user handle 18, shown in FIG. 1. Catheter 130 includes an elongated, helical coil spring 136 that encloses a longitudinally extending passageway. In a terminal portion 138 of coil spring 136 adjoining the distal end thereof, successive loops of coil spring 136 are longitudinally separated. Proximal of terminal portion 138 successive loops of coil spring 136 are bottomed out.

A flexible tube 140 snugly engages the exterior of coil spring 136. Flexible tube 140 includes an inner layer 142 that is in direct contact with the exterior of coil spring 136 and an outer layer 144 engaging the exterior of inner layer 142. Inner layer 142 stops proximal terminal portion 138 of coil spring 136, where successive loops of coil spring 136 are bottomed out. Typically, outer layer 144 is softer and more skin compatible than is inner layer 142. Coil spring 136 and flexible tube 140 together function for catheter 130 as an elongated tubular outer wall that is internally reinforced by a helical coil spring. In various embodiments, eye-holes or eyelets 139 are cut or formed in flexible tube 140 for infusion along terminal portion 138.

According to one aspect of the invention, a catheter, such as catheter 130, includes utility enhancement means operably interconnected with the outer wall of that catheter for both longitudinally rigidifying the outer wall and for selectively laterally deflecting the distal tip of the catheter. As illustrated in FIG. 10 by way of example and not limitation, catheter 130 includes a continuous filament 146 having a bound portion 148 extending longitudinally of catheter 130 along the exterior of coil spring 136. Bound portion 148 has a distal end 150 that is disposed in proximity to the distal end of coil spring 136. Filament 146 also includes a free portion 152 having a distal end 154 that is joined to distal end 150 of bound portion 148. As shown in FIG. 10, bound portion 148 and free portion 152 are so joined at the distal ends thereof as to be a single continuous filament, although other manners of effecting that connection directly or through intermediating structures would be consistent with teachings of the invention. The withdrawal of free portion 152 of filament 146 proximally through the working lumen in catheter 130 as indicated by an arrow $W_3$ causes distal tip 132 of catheter 130 to be deflected to the right in a direction indicated by an arrow an $D_3$.

If it is intended to deflect distal tip 132 in the opposite direction, to the left in FIG. 10, distal tip 132 of catheter 130 is first rotated by 180° through the application of twisting forces to the proximal end of catheter 130. Then the retraction of free portion 152 of filament 146 through the working lumen in catheter 130 in the direction of arrow $W_3$ will cause distal tip 132 to be deflected to the left in FIG. 10.

A rigid end piece 156 is secured to distal end 158 of flexible tube 140. In various embodiments, end piece 156 is welded, such as in a welded ball, to distal end 158 and/or to coil spring 136 and/or to filament 146. End piece 156, functions as a closed distal terminus for the working lumen within catheter 130 and has a semispherical exterior profile. An electrically driven transducer 160 is mounted in end piece 156 and coupled to power and control sources at the proximal end of catheter 130 through a lead wire 162 that extends from transducer 160 proximally through the working lumen in catheter 130. End piece 156 can also function as an attachment site as for continuous filament 146.

Figure 11:
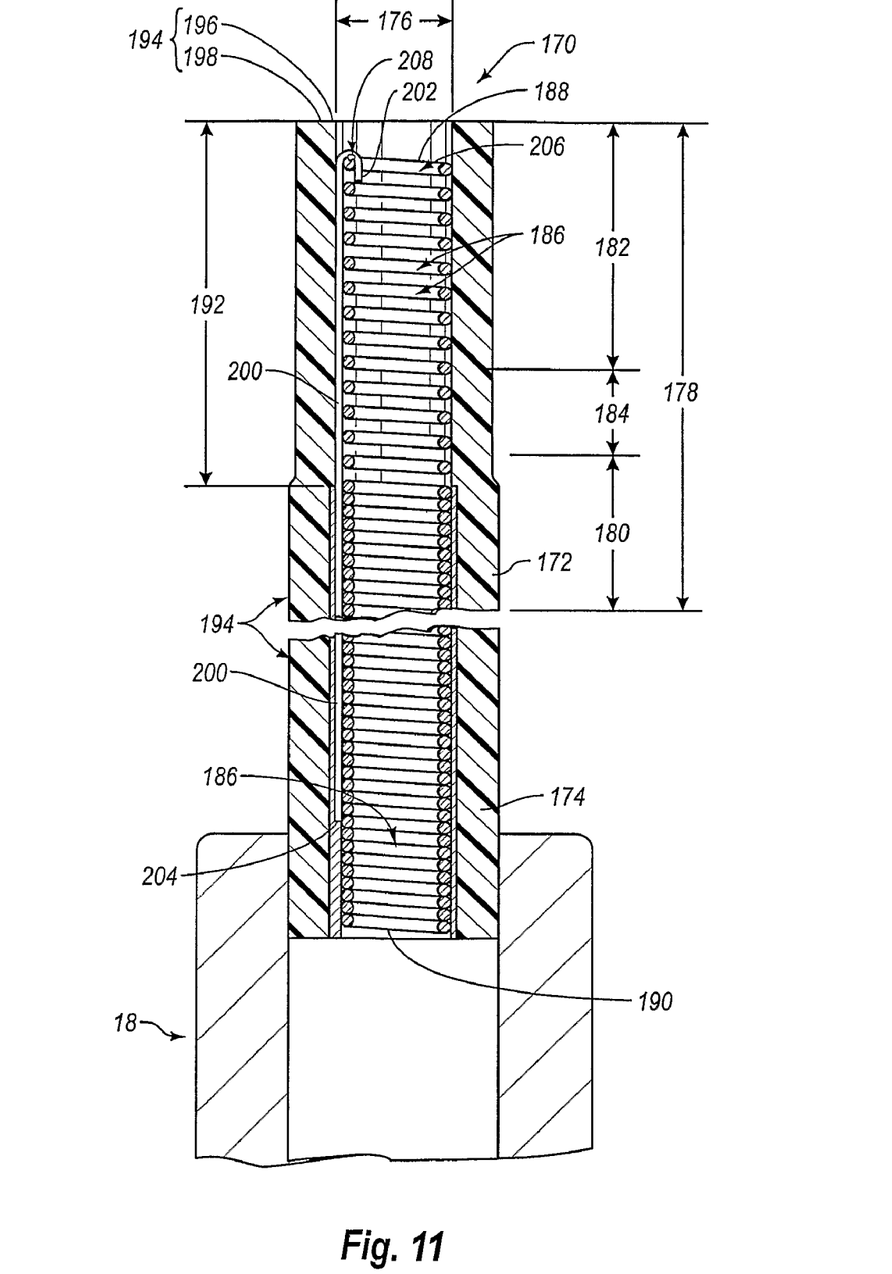
FIG. 11 is a longitudinal cross section of the distal and proximal ends of a nonarticulated fourth embodiment of a catheter incorporating teachings of the invention.
Figure 12A:
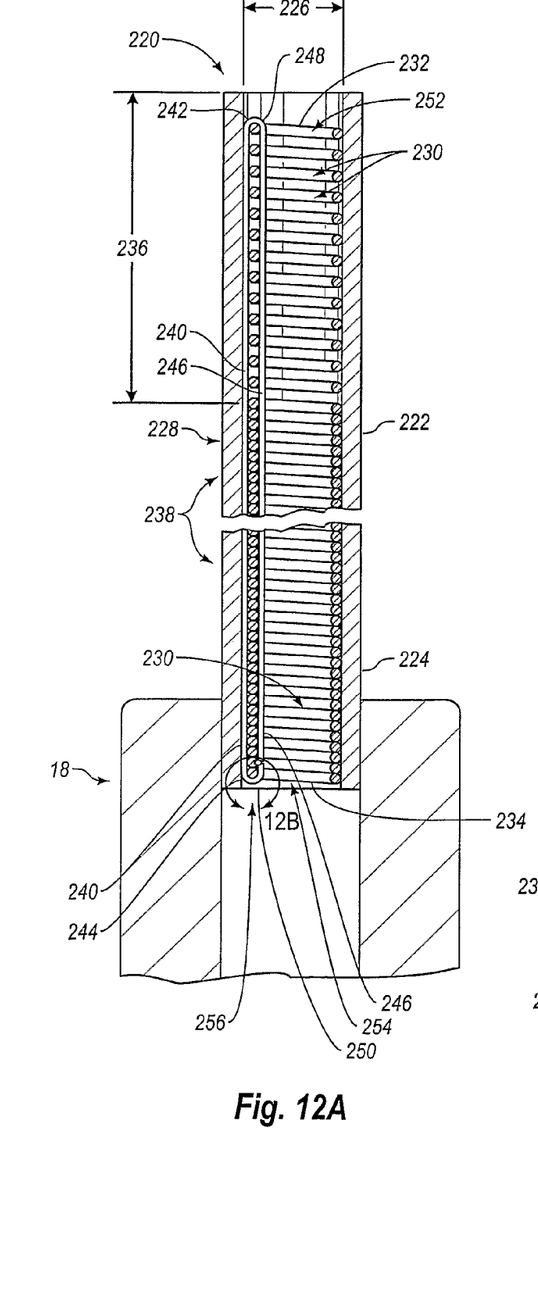
FIG. 12A is a transverse cross section of the distal and proximal ends of a nonarticulated fifth embodiment of a catheter incorporating teachings of the invention.
Figure 12B:
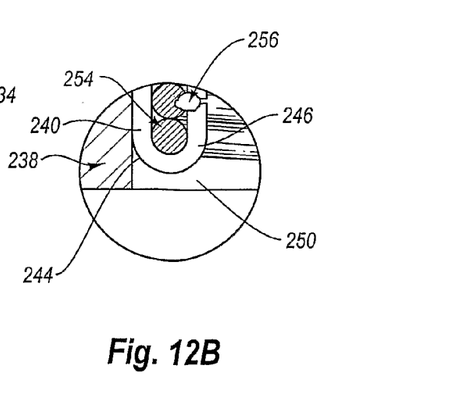
FIG. 12B is an enlarged detailed view of a portion of the catheter of FIG. 12A.

Teachings of the invention find applicability in addition in the construction of reinforced catheter tubing that is intended for use with catheters without articulated distal tips. FIGS. 11 and 12 depict embodiments of such reinforced, non-articulated catheters incorporating teachings of the invention.

FIG. 11 depicts a fourth embodiment of a catheter 170 that has been longitudinally reinforced according to teachings of the invention. Catheter 170 has an open distal end 172, an open proximal end 174, and a working lumen extending longitudinally therebetween that communicates with the exterior of catheter 170 at distal end 172 through an end opening 176. Proximal end 174 of catheter 170 is secured to a user handle 18. Catheter 170 includes a distal tip 178 that exhibits a two-stage outer profile, including a large diameter proximal portion 180 and a small diameter distal portion 182 with exterior surfaces smoothly interconnected by an intermediate transition portion 184.

The interior construction of catheter 170 involves an elongated helical coil spring 186 having an open distal end 188 and an open proximal end 190 and enclosing a longitudinal passageway extending therebetween. In a terminal portion 192 of coil spring 186 adjoining distal end 188 thereof, successive loops of coil spring 186 are longitudinally separated. Successive loops of coil spring 186 proximal of terminal portion 192 are bottomed out.

An elongated flexible tube 194 snugly engages the exterior of coil spring 186 along the full length of catheter 170. Flexible tube 194 includes an inner layer 196 that is in direct contact with the exterior of coil spring 186 and an outer layer 198 that engages the exterior of inner layer 196. Often, outer layer 198 is manufactured from a softer more skin-compatible material than that utilized in forming inner layer 196. Inner layer 196 has a uniform thickness and, an invariable outer diameter along the full length of catheter 170. The thickness of outer layer 198 increases in the proximal direction at transition portion 184 and is therefore greater in distal portion 182 of distal tip 178 than in proximal portion 180.

To enhance the longitudinal rigidity of catheter 170 and/or enhance fluoroscopic visibility, one or more longitudinally extending reinforcing cables 200 are disposed between flexible tube 194 and the exterior of coil spring 186. The single reinforcing cable 200 illustrated in FIG. 11, has a distal end 202 disposed in proximity to distal end 188 of coil spring 186 and a proximal end 204. Reinforcing cable 200 is captured between flexible tube 194 and coil spring 186 by the grip of flexible tube 194 on the exterior of coil spring 186, or reinforcing cable 200 may be adhered to either of these structures. Distal end 202 of reinforcing cable 200 is shown by way of illustration to be secured to final loop 206 of coil spring 186 at a bonding site 208. Proximal end 204 of reinforcing cable 200 does not extend the full length of catheter 170 and is thus captured between flexible tube 194 and coil spring 186 distal of proximal end 190 of coil spring 186.

Coil spring 186 and flexible tube 194 together function in catheter 170 as an elongated tubular outer wall reinforced by an internal helical coil spring. This tubular outer wall encloses the working lumen for catheter 170. The disposition of one or more reinforcing cables, like reinforcing cable 200, within that elongated tubular outer wall between flexible tube 194 and coil spring 186 lends to catheter 170 an enhanced capacity to transmit to distal end 172 thereof advancement, withdrawal, and twisting forces applied to proximal end 174 by a user.

FIGS. 12A and 12B depict a fourth embodiment of a catheter 220 that has been longitudinally reinforced according to teachings of the invention. Catheter 220 has an open distal end 222, an open proximal end 224, and a working lumen that extends longitudinally therebetween and communicates with the exterior of catheter 220 at distal end 222 through an end opening 226. Proximal end 224 of catheter 220 is secured to a user handler 18. Catheter 220 includes a distal tip 228 that has an outer diameter of unchanging size.

The interior construction of catheter 220 involves an elongated helical coil spring 230 having an open distal end 232 and an open proximal end 234 and enclosing a longitudinal passageway extending therebetween. In a terminal portion 236 of coil spring 230 adjoining distal end 232 thereof, successive loops of coil spring 230 are longitudinally separated. The successive loops of coil spring 230 proximal of terminal portion 236 thereof are bottomed out.

An elongated flexible tube 238 snugly encircles the exterior of coil spring 230 along the full length of catheter 220. Flexible tube 238 exhibits a single-layer structure of substantially uniform material composition. Coil spring 230 and flexible tube 238 together function in catheter 220 as an elongated tubular outer wall reinforced by an internal helical spring coil. That outer wall encloses the working lumen that extends longitudinally through catheter 220 from distal end 222 to proximal end 224 thereof.

To enhance the longitudinal rigidity of catheter 220, one or more pairs of longitudinally extending reinforcing cables of the type illustrated in FIG. 12A are integrated into the structure of catheter 220. A first reinforcing cable 240 having a distal end 242 disposed proximate to distal end 232 of coil spring 230 and a proximal end 244 is disposed proximate to proximal end 234 of coil spring 230 is located between flexible tube 238 and the exterior of coil spring 230. First reinforcing cable 240 is thus captured between flexible tube 238 and the exterior of coil spring 230 or adhered to either of these structures.

A second reinforcing cable 246 having a distal end 248 and a proximal end 250 extends the full length of coil spring 230 from distal end 232 to proximal end 234 of coil spring 230 within the working lumen in catheter 220. Distal end 242 of first reinforcing cable 240 and distal end 248 of second reinforcing cable 246 are attached directly in a smoothly continuous manner, whereby first reinforcing cable 240 and second reinforcing cable 246 form a continuous elongated structure. Nonetheless, first reinforcing cable 240 and second reinforcing cable 246 could be distinctly different structures with attached distal ends or, with operably interconnected distal ends, as by being bonded to final distal loop 252 of coil spring 230.

As shown with enhanced clarity in FIG. 12B, at final proximal loop 254 of coil spring 230 proximal end 244 of first reinforcing cable 240 and proximal end 250 of second reinforcing cable 246 are secured to each other at a bonding site 256. Alternatively, each of proximal end 244 of first reinforcing cable 240 and proximal end 250 of second reinforcing cable 246 can be secured directly to final proximal loop 254 of coil spring 230. In any case, the attachment of proximal end 250 of second reinforcing cable 246 serves to position second reinforcing cable 246 in contact with the interior surface of coil spring 230 when catheter 220 is unbent as in FIG. 12A.

The disposition of one or more pairs of reinforcing cables like first reinforcing cable 240 within that elongated tubular outer wall of catheter 220 and second reinforcing cable 246 within the working lumen in that elongated tubular outer wall, lends to catheter 220 an enhanced capacity to transmit to distal end 222 thereof advancement, withdrawal, and twisting forces applied to proximal end 224 by a user. Such pairs of reinforcing cables also serve to maintain the position in catheter 220 of loops of spring coil 230 should flexible tube 238 cease to be able to do so due to wear or fracture.

The invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A catheter with an articulated distal tip, said catheter comprising:
    an elongated, helical coil spring having open distal and proximal ends and enclosing a longitudinal passageway extending therebetween, successive loops of said coil spring in a terminal portion of said coil spring adjoining said distal end thereof being longitudinally separated;
    an elongated flexible tube having open distal and proximal ends snugly engaging the exterior of said coil spring, the combination of said flexible tube and said coil spring thereby laterally enclosing a working lumen extending longitudinally through said catheter; and
    utility enhancement means operably interconnected with said coil spring and with said flexible tube for longitudinally rigidifying said combination of said flexible tube and said coil spring and for selectively laterally deflecting the distal tip of said catheter, wherein the utility enhancement means comprises:
        a longitudinally extending reinforcing cable captured against the exterior of the coil spring, the distal end of the reinforcing cable being disposed in proximity to the distal end of the coil spring; and
        a steering cable having a distal end operably interconnected with the distal end of the coil spring, the steering cable extending proximally from the distal end thereof freely through the working lumen to the proximal end of the catheter.

2. A catheter with an articulated distal tip, said catheter comprising:
    an elongated tubular outer wall reinforced by an internal helical coil spring having open distal and proximal ends, said outer wall having open distal and proximal ends and enclosing a working lumen extending longitudinally through said catheter, successive loops of said coil spring in a terminal portion of said coil spring adjoining said distal end thereof being longitudinally separated; and
    utility enhancement means operably interconnected with said outer wall for longitudinally rigidifying said outer wall and for selectively laterally deflecting the distal tip of said catheter wherein the utility enhancement means comprises a continuous filament, the continuous filament comprising:
        a bound portion extending longitudinally of the catheter against the exterior of the coil spring, the distal end of the bound portion being disposed in proximity to the distal end of the coil spring; and
        a free portion having a distal end joined in a smoothly continuous manner to the distal end of the bound portion, the free portion of the filament extending proximally from the distal end thereof freely through the working lumen to the proximal end of the catheter.

3. A catheter with an articulated distal tip, the catheter comprising:
    an elongated tubular outer wall reinforced by an internal helical coil spring having open distal and proximal ends, the outer wall having open distal and proximal ends and enclosing a working lumen extending longitudinally through the catheter, successive loops of the coil spring in a terminal portion of the coil spring adjoining the distal end thereof being longitudinally separated;
    utility enhancement means operably interconnected with the outer wall for longitudinally rigidifying the outer wall and for selectively laterally deflecting the distal tip of the catheter; and
    a rigid end piece at said distal end of said outer wall.

4. The catheter of claim 3, wherein said end piece comprises a ring coaxially disposed relative to said working lumen.

5. The catheter of claim 3, wherein said end piece comprises a closed distal terminus for said working lumen.

6. The catheter of claim 5, wherein said end piece has a semispherical exterior profile.

7. The catheter of claim 3, further comprising an electrical transducer carried by said end piece, said transducer being capable of selectively performing therapeutic medical functions within the body of a patient or subject.

8. A catheter with an articulated distal tip, said catheter comprising:
    an elongated tubular outer wall reinforced by an internal helical coil spring having open distal and proximal ends, said outer wall having open distal and proximal ends and enclosing a working lumen extending longitudinally through said catheter, successive loops of said coil spring in a terminal portion of said coil spring adjoining said distal end thereof being longitudinally separated;
    a longitudinally extending reinforcing cable captured against the exterior of said coil spring, the distal end of said reinforcing cable being disposed in proximity to said distal end of said coil spring;
    a steering cable having a distal end operably interconnected with said distal end of said coil spring, said steering cable extending proximally from said distal end thereof freely through said working lumen to the proximal end of said catheter; and
    a rigid end piece secured to said distal end of said outer wall.

9. The catheter of claim 8, wherein said reinforcing cable and said steering cable comprise a continuous elongated structure.

10. The catheter of claim 8, wherein said outer wall comprises a flexible tube having open distal and proximal ends and snugly engaging the exterior of said coil spring.

11. A catheter with an articulated distal tip, said catheter comprising:
    an elongated tubular outer wall reinforced by an internal helical coil spring having open distal and proximal ends, said outer wall having open distal and proximal ends and enclosing a working lumen extending longitudinally through said catheter, successive loops of said coil spring in a terminal portion of said coil spring adjoining said distal end thereof being longitudinally separated;
    a longitudinally extending reinforcing cable captured against the exterior of said coil spring, the distal end of said reinforcing cable being disposed in proximity to said distal end of said coil spring;
    a steering cable having a distal end operably interconnected with said distal end of said coil spring, said steering cable extending proximally from said distal end thereof freely through said working lumen to the proximal end of said catheter;

a handle attached to said proximal end of said outer wall; and control means in said handle operably interconnected with the proximal end of said steering cable for drawing said proximal end of said steering cable proximally of said catheter.

12. The catheter of claim 11, further comprising a rigid ring coaxially disposed relative to said working lumen at said distal end of said outer wall.

13. The catheter of claim 11, further comprising a closed distal terminus for said working lumen, said distal terminus having a semispherical exterior profile.

14. The catheter of claim 11, wherein said outer wall comprises a flexible tube having open distal and proximal ends and snugly engaging the exterior of said coil spring.

15. A catheter tube comprising:

an elongated, helical coil spring having open distal and proximal ends and enclosing a longitudinal passageway extending therebetween, successive loops of said coil spring in a terminal portion of said coil spring adjoining said distal end thereof being longitudinally separated;

an elongated flexible tube having open distal and proximal ends and snugly engaging the exterior of said coil spring, the combination of said flexible tube and said spring coil thereby laterally enclosing a working lumen extending longitudinally through said catheter tube; and a longitudinally extending reinforcing cable captured between said flexible tube and said exterior of said coil spring.

16. A catheter tube comprising:

an elongated tubular outer wall reinforced by an internal helical coil spring having open distal end and proximal ends, said outer wall having open distal and proximal ends and enclosing a working lumen extending longitudinally through said catheter tube, successive loops of said coil spring in a terminal portion of said coil spring adjoining said distal end thereof being longitudinally separated;

a longitudinally extending first reinforcing cable captured against the exterior of said coil spring, the distal end of said first reinforcing cable being disposed in proximity to said distal end of said coil spring, and the proximal end of said first reinforcing cable being disposed in proximity to said proximal end of said coil spring; and a second reinforcing cable having a distal end secured to said distal end of said first reinforcing cable, said second reinforcing cable extending proximally from said distal end thereof through said working lumen, and the proximal end of said second reinforcing cable being secured to said proximal end of said first reinforcing cable.

17. The catheter tube of claim 16, wherein said distal end of said first reinforcing cable and the distal end of said second reinforcing cable are joined in a smoothly continuous manner.

18. The catheter of claim 1, wherein said distal end of said steering cable is secured to said distal end of said reinforcing cable.

19. A catheter with an articulated distal tip, the catheter comprising:

an elongated, helical coil spring having open distal and proximal ends and enclosing a longitudinal passageway extending therebetween, successive loops of the coil spring in a terminal portion of the coil spring adjoining the distal end thereof being longitudinally separated, wherein successive loops of said coil spring proximal of said terminal portion thereof are bottomed out;

an elongated flexible tube having open distal and proximal ends snugly engaging the exterior of the coil spring, the combination of the flexible tube and the coil spring thereby laterally enclosing a working lumen extending longitudinally through the catheter; and utility enhancement means operably interconnected with the coil spring and with the flexible tube for longitudinally rigidifying the combination of the flexible tube and the coil spring and for selectively laterally deflecting the distal tip of the catheter.

20. A catheter with an articulated distal tip, the catheter comprising:

an elongated, helical coil spring having open distal and proximal ends and enclosing a longitudinal passageway extending therebetween, successive loops of the coil spring in a terminal portion of the coil spring adjoining the distal end thereof being longitudinally separated;

an elongated flexible tube having open distal and proximal ends snugly engaging the exterior of the coil spring, the combination of the flexible tube and the coil spring thereby laterally enclosing a working lumen extending longitudinally through the catheter, wherein said flexible tube comprises:

an inner layer disposed in direct contact with said exterior of said coil spring; and an outer layer engaging the exterior of said inner layer, said outer layer being softer than said inner layer; and utility enhancement means operably interconnected with the coil spring and with the flexible tube for longitudinally rigidifying the combination of the flexible tube and the coil spring and for selectively laterally deflecting the distal tip of the catheter.

21. The catheter of claim 20, wherein a terminal portion of said outer layer of said flexible tube adjoining said distal end of said flexible tube is softer than said outer layer proximal of said terminal portion thereof.

22. A method for manufacturing a catheter with an articulated distal tip, the method comprising:

providing an elongated, helical coil spring having open distal and proximal ends and enclosing a longitudinal passageway extending therebetween, successive loops of the coil spring in a distal portion of the coil spring adjoining the distal end thereof being longitudinally separated;

disposing a first portion of a filament along the exterior of the coil spring with a second portion of the filament extending distally beyond the distal end of the coil spring;

passing the end of the second portion of the filament remote from the first portion through the passageway in the coil spring from the distal end to the proximal end thereof; and snugly engaging a flexible tube about the exterior of the coil spring and the first portion of the filament.

23. The method according to claim 22, further comprising attaching a rigid end piece to the distal end of the flexible tube.

24. The method according to claim 23, further comprising installing an electrically activated transducer on the rigid end piece.

25. The method according to claim 22, further comprising securing a handle to the proximal end of the flexible tube.

* * * * *